United States Patent [19]

Walsh

[11] Patent Number: 4,994,051
[45] Date of Patent: Feb. 19, 1991

[54] EXTERNAL URINE CATHETER FOR MALES

[76] Inventor: Leopoldine Walsh, R.D. 1, Box 1-Bryun Tpk., Wallkil, N.Y. 12589

[21] Appl. No.: 454,933

[22] Filed: Dec. 22, 1989

[51] Int. Cl.⁵ .............................................. A61F 5/44
[52] U.S. Cl. .................................... 604/349; 604/353
[58] Field of Search ............................... 604/349, 363

[56] References Cited

U.S. PATENT DOCUMENTS

| | | | |
|---|---|---|---|
| 3,032,038 | 5/1962 | Swinn | 604/353 |
| 4,073,295 | 2/1978 | Laufbahr | 604/353 |
| 4,387,726 | 6/1983 | Denarde | 604/349 |
| 4,531,245 | 7/1985 | Lowd et al. | 604/349 |
| 4,588,397 | 5/1985 | Giacalone | 604/349 |
| 4,713,066 | 3/1986 | Komis | 604/349 |
| 4,713,067 | 12/1987 | Rothenberg et al. | 604/349 |
| 4,820,291 | 7/1987 | Teranchi et al. | 604/349 |
| 4,846,816 | 7/1989 | Manfredi | 604/349 |

Primary Examiner—Randall L. Green
Assistant Examiner—Robert Clarke
Attorney, Agent, or Firm—Iman Abdallah

[57] ABSTRACT

An external catheter system for males including a waist belt assembly, a genital sheath having a scrotum bar, and a urine collector, wherein the sheath and urine collector are interconnected by a length of flexible tubing. The urine collector provides means for collection of expelled urine and means to stage and treat expelled urine prior to ultimate disposal.

10 Claims, 3 Drawing Sheets

EXTERNAL URINE CATHETER FOR MALES

BACKGROUND OF THE INVENTION

The present invention generally relates to urine collection devices. More specifically the invention of the present disclosure relates to external urine catheters for males.

Various devices are known in the prior art for collecting voluntary and incontinent urination. Such devices include internal catheters which extend into the urethra to drain urine from the bladder, and external catheters which, for example, surround the penis of a male. Internal catheters in particular may cause urinary tract infections and kidney problems and therefore their usefulness is generally limited to short-term use. External catheters have shown greater utility for long-term use but present leakage and hygiene problems. External catheters also can produce sores from rubbing against the groin of the user. Several inventions in the prior art have been identified by the Applicant as pertinent to the present disclosure which address the recognized problems of leakage and sanitation. In U.S. Pat. No. 3,035,579 to Benovic a urine retaining device is disclosed which includes a flexible waistband having a flexible bag member attached thereto by respective pairs of adjustable flexible strap members disposed to each side of said bag member, said bag member being adapted to receive the male organs. The bag member includes inner and outer receptacles shaped to generally conform with the contour of the male organs between which is disposed removable absorbent material. The inner receptacle has a notch formed at its upper forward portion for receipt of the penis forming an opening which communicates with the space between the inner and outer receptacles. The portion of the inner receptacle below said notch forms a wall between the penis and the scrotum. In U.S. Pat. No. 4,387,726 to Denard a disposable urine collection device is disclosed which similarly attaches to the body via a waist belt and includes a urine collecting structure comprising a double cylinder container. The penis is inserted into the inner cylinder and expelled urine is collected and stored in the outer cylinder. An external catheter particularly directed to the prevention of urine leakage is disclosed in U.S. Pat. No. 4,588,397 to Giacalone. In the Giacalone invention a nether garment having a sealingly attachable tubular sheath is described wherein the sealing means comprises an annular neck and collar assembly. In U.S. Pat. No. 4,531,245 to Lowd et al. a portable personal urinal device is disclosed which may be utilized by females or males. The urinal device of this invention generally comprises an upper bowl member and lower collector member, the collector member being formed in a manner permitting selective discharge of collected urine.

While the above-mentioned inventions are not exhaustive of the prior art, these inventions illustrate the scope of the prior art which does not meet the objectives of the present invention.

SUMMARY OF THE INVENTION

An object of the present invention is to provide an external catheter suitable for long-term use.

It is also an object of this invention to provide a urine collection device that prevents soiling and staining of body or bed clothes.

Another object of the present invention is to provide a collection device for voluntary and incontinent urination which reduces the potential for the development of urinary tract infections and kidney problems.

A further object of the present invention is to provide an external urine catheter which permits collection of urine away from the body of the user.

A still further object of the present invention is to provide an external urine catheter system which provides means for collected urine to be staged and treated prior to disposal.

It is also an object of this invention to provide an external catheter of simple construction including an adjustable waist belt assembly which prevents the device from slipping away from the body during normal movement of the user.

These and other objects and advantages of the present invention will be apparent to those skilled in the art from the following description of a preferred embodiment and claims, and from the accompanying drawings, wherein there is disclosed an external urine catheter system for males including a substantially tubular sheath for receipt of the male genitalia, a waist belt assembly selectively attachable to said sheath, a urine collector suitable for staging and treatment of collected urine prior to ultimate disposal, and sheath draining tubing which interconnects said sheath and said urine collector.

DESCRIPTION OF A PREFERRED EMBODIMENT

Figure 1:
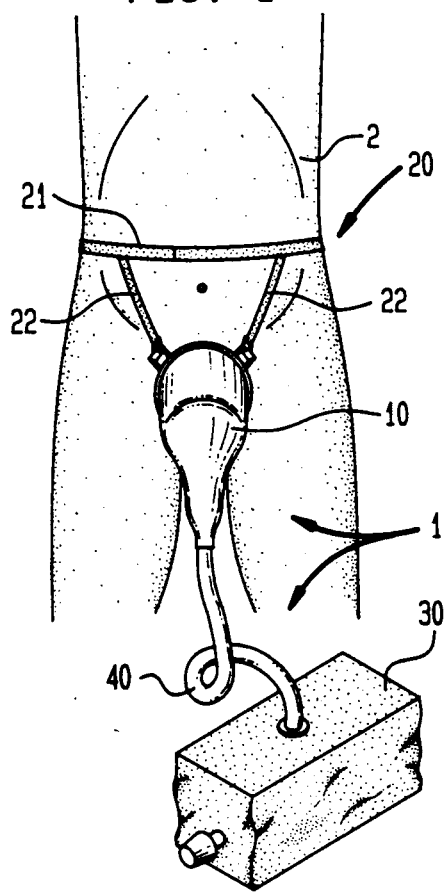
FIG. 1 is a front elevational view of the external catheter system of the present invention shown as worn by a human male.
Figure 2:
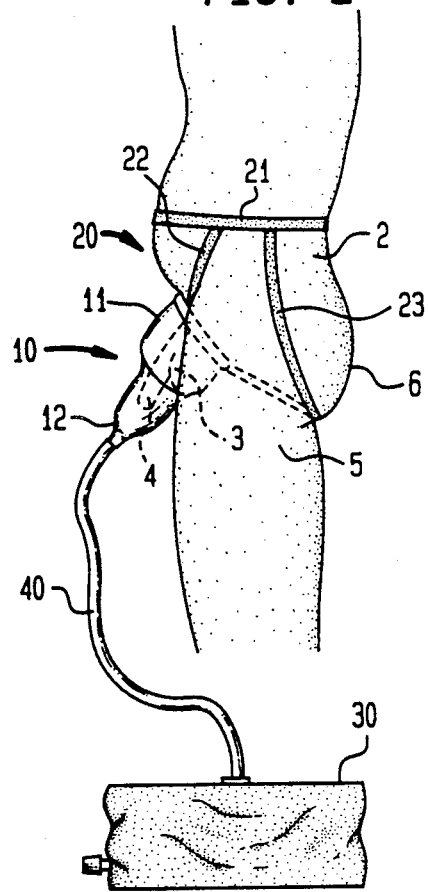
FIG. 2 is a side elevational view of the external catheter shown in FIG. 1.

FIG. 1 illustrates in a front elevational view the first preferred embodiment of the external urine catheter system 1 of the present invention. The external catheter system 1 is adapted to fit and be worn around the waist and the lower part of the abdomen of a human male body 2 and generally includes a substantially tubular sheath 10 for receipt of the male genitalia, a waist belt assembly 20 selectively attachable to said sheath 10, a urine collector 30, and a length of hollow sheath draining tubing 40 which interconnects said sheath 10 and said urine collector 30. As can be seen in FIG. 2 the tubular sheath 10 includes an upper portion 11 adapted to fit adjacent to the pubic area of the user's body 2 and a lower portion 12 of smaller diameter integrally formed at the distal end of the upper portion 11 of said sheath 10. The upper portion 11 of sheath 10 provides a support structure for the male scrotum 3 and the lower portion 12 of sheath 10 provides a structure for receipt of the male penis 4. Waist belt assembly 20 includes a selectively adjustable waist belt 21, a pair of frontal sheath straps 22 fixedly attached at one end to said waist belt 21 and selectively attachable at the opposite end to the top proximal edge of said sheath 10, and a pair of thigh straps 23 fixedly attached at one end to said waist belt 21 and selectively attachable at the opposite end to the bottom proximal edge of said sheath 10. Thigh straps 23 are disposed to fit around the thighs 5 of the user's body 2 passing below the user's buttocks 6 and between the user's crotch.

Figure 3:
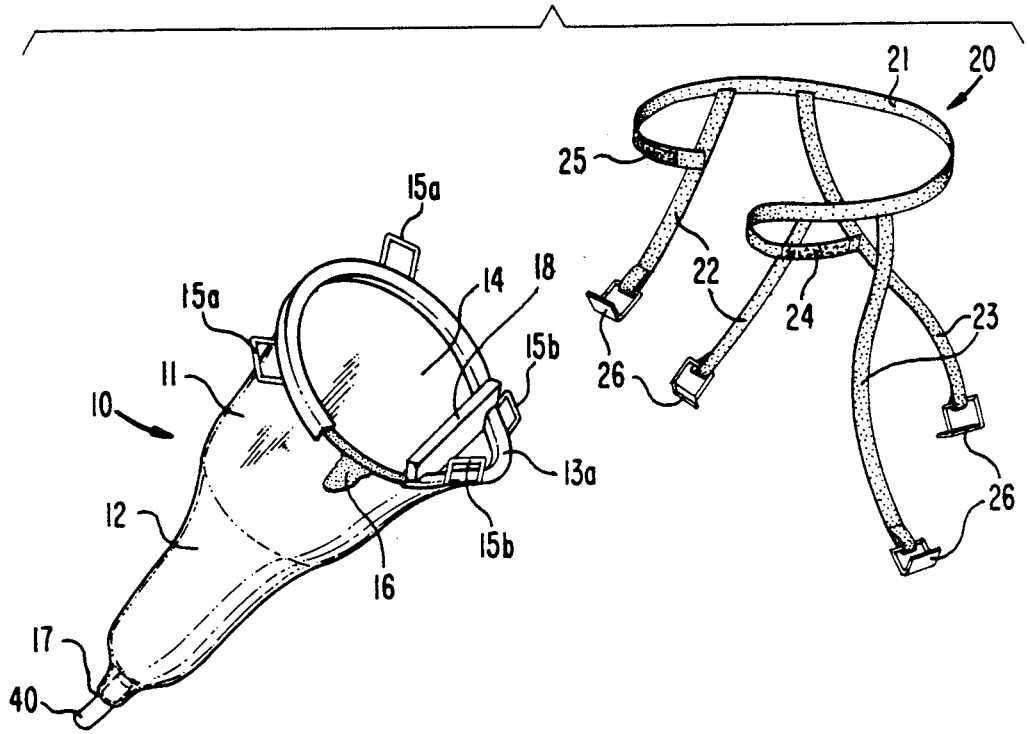
FIG. 3 is an enlarged perspective view of the waist belt assembly and tubular sheath of the preferred embodiment.

Referring now to FIG. 3 there is shown in greater detail the waist belt assembly 20 and sheath 10 of the preferred embodiment of the present invention. The preferred embodiment of waist belt assembly 20 comprises a unitary construction of belts and straps including a waist belt 21, a pair of frontal sheath straps 22 and a pair of thigh straps 23 respectively disposed forwardly and rearwardly on each side of said waist belt 21. Waist belt 21 is preferably formed from resilient elastic material which can be stretched longitudinally to fit varying waist sizes. Frontal sheath straps 22 and thigh straps 23 are likewise formed from similar resilient elastic material. A hook and loop tape fastener is fixedly attached to the free ends of the waist belt 21, the hook portion 24 being attached to the inside surface of one end of the waist belt 21 and the loop portion 25 being attached to the outside surface of the other end of the waist belt 21, such construction permitting the waist belt 21 to be adjustably fastened about the waist of the user. Frontal sheath straps 22 and thigh straps 23 are fixedly attached at one end to the inside surface of the waist belt 21, for example by stitching. Frontal sheath straps 22 are attached to the forward side portions of waist belt 21 extending angularly toward the front of waist belt assembly 20 and thigh straps 23 are attached to the rearward side portions of the waist belt 21 extending angularly toward the rear of waist belt assembly 20. The free ends of frontal sheath straps 22 and thigh straps 23 are looped and stitched to form a closed loop wherein attachment clips 26 are disposed for engagement with attachment tabs 15a, 15b formed on said sheath 10 as hereinafter described. Attachment clips 26 are preferably formed of plastic or similar lightweight material.

Sheath 10 is shown in FIG. 3 with a portion of said upper portion 11 cut away to reveal the various layers of sheath 10. Sheath 10 is a substantially tubular member, preferably formed from rigid plastic material, the upper portion 11 having a larger diameter than lower portion 12. Upper portion 11 is generally formed in the shape of a bottomless cup having an arcuate lip 13 circumscribing an opening 14 provided for receipt of the male genitalia, said opening 14 extending longitudinally throughout said sheath 10. A lip prolongation 13a forms one side of said lip 13 and extends outwardly from the upper portion 11 of said sheath 10. When sheath 10 is worn the lip prolongation 13a protrudes into the crotch of the user. A scrotum bar 18, preferably formed from soft rubber or other flexible dense material, extends laterally across the lower part of lip 13 adjacent lip prolongation 13a. The genitals of a sick or immobile person that is not sexually active tend to draw within the body. The scrotum bar 18 facilitates the prevention of this withdrawal into the body so that the catheter system 1 retains its utility in such instances. Pairs of upper and lower attachment tabs 15a, 15b extend outwardly from lip 13, said upper attachment tabs 15a extending from the upper sides of lip 13 and said lower attachment tabs 15b extending from the sides of lip prolongation 13b. Upper attachment tabs 15a are provided for engagement of the attachment clips 26 of said frontal sheath straps 22, and lower attachment tabs 15b are provided for engagement of the attachment clips 26 of said thigh straps 23. Foam padding 16 is disposed within the sheath 10 conforming throughout to the contours of sheath 10. The lower portion 12 of sheath 10 is integrally formed at the distal end of upper portion 11 and generally comprises an elongated cylinder having a diameter that decreases from its adjoining portion to its end portion. The opening 14 extends to an orifice 17 formed at the end portion of said sheath lower portion 12, said orifice 17 being adapted to receive in snug engagement an end of said sheath draining tubing 40.

Figure 4:
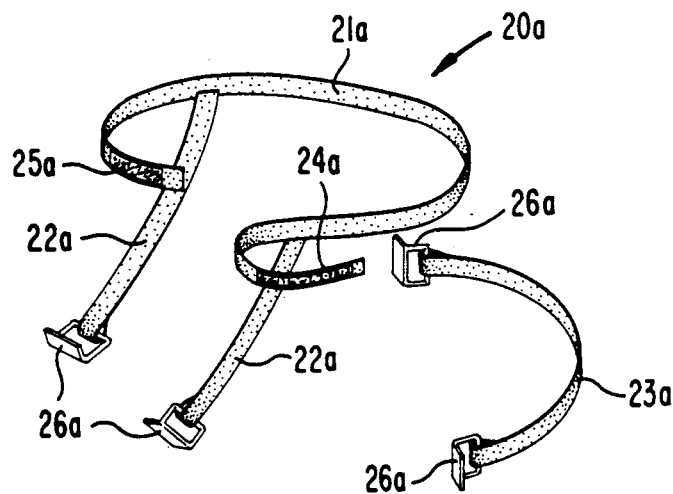
FIG. 4 is a perspective view of an alternative embodiment of the waist belt assembly of the present invention.

The waist belt assembly 20 of the preferred embodiment may be alternatively formed as a two-piece construction as shown in FIG. 4. The alternative embodiment of waist belt assembly 20a includes a waist belt 21a, and a pair of frontal sheath straps 22a respectively disposed on each side of said waist belt 21a and fixedly attached thereto. A separate and singular thigh strap 23a is provided that is adaptable to be worn about the outer portions of the thighs and below the buttocks of the user. When the alternative embodiment of waist belt assembly 20a is used the lower attachment tabs 15b of sheath 10 must be constructed on the lower portion of lip 13 rather than on lip prolongation 13a and must be outwardly disposed at a different angle from said sheath 10. Waist belt 21a, frontal sheath straps 22a and thigh strap 23a are formed from similar resilient elastic material as described for the belt and straps of the first preferred embodiment shown in FIGS. 1-3. Attachment clips 26a and belt fastener means 24a, 25a are disposed and attached as described for the preferred embodiment.

Figure 5:
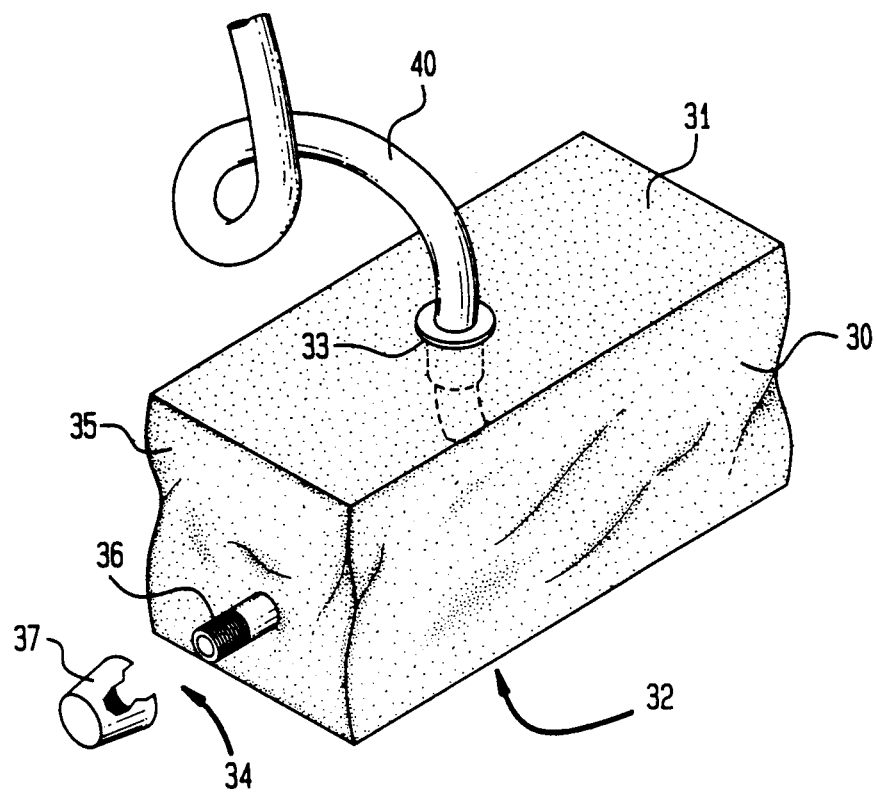
FIG. 5 is a perspective view of the urine collector of the present invention.

Referring now to FIG. 5, a perspective view of the urine collector 30 is shown with the distal end of said sheath draining tubing 40 attached thereto. Urine collector 30 is substantially a flexible box member having a rigid top member 31 to facilitate draining of the sheath 10 and a rigid bottom member 32 to facilitate upright positioning of the collector 30. A urine inlet receptacle 33 is formed in the top member 31 of said collector 30 for receipt of the sheath draining tubing 40 in sealingly engagement A collector disposal port 34 is formed in the side wall 35 of the collector, said disposal port 34 comprising a threaded port neck 36 and a complementarily threaded port neck cap 37, said cap 37 being provided to selectively seal the disposal port 34. Urine collector 30 not only provides means for collection of urine from sheath 10 but also provides means for staging collected urine for treatment prior to ultimate disposal. For example, water or disinfectant may be retained in collector 30 to dilute or treat collected urine. Such construction reduces odor, disease transmission and sanitation problems associated with external catheters. Dry or liquid disinfectant may be utilized. Alternatively, cleaning fluids may be retained in the collector 30 to facilitate maintenance of the external catheter system 1.

Figure 6:
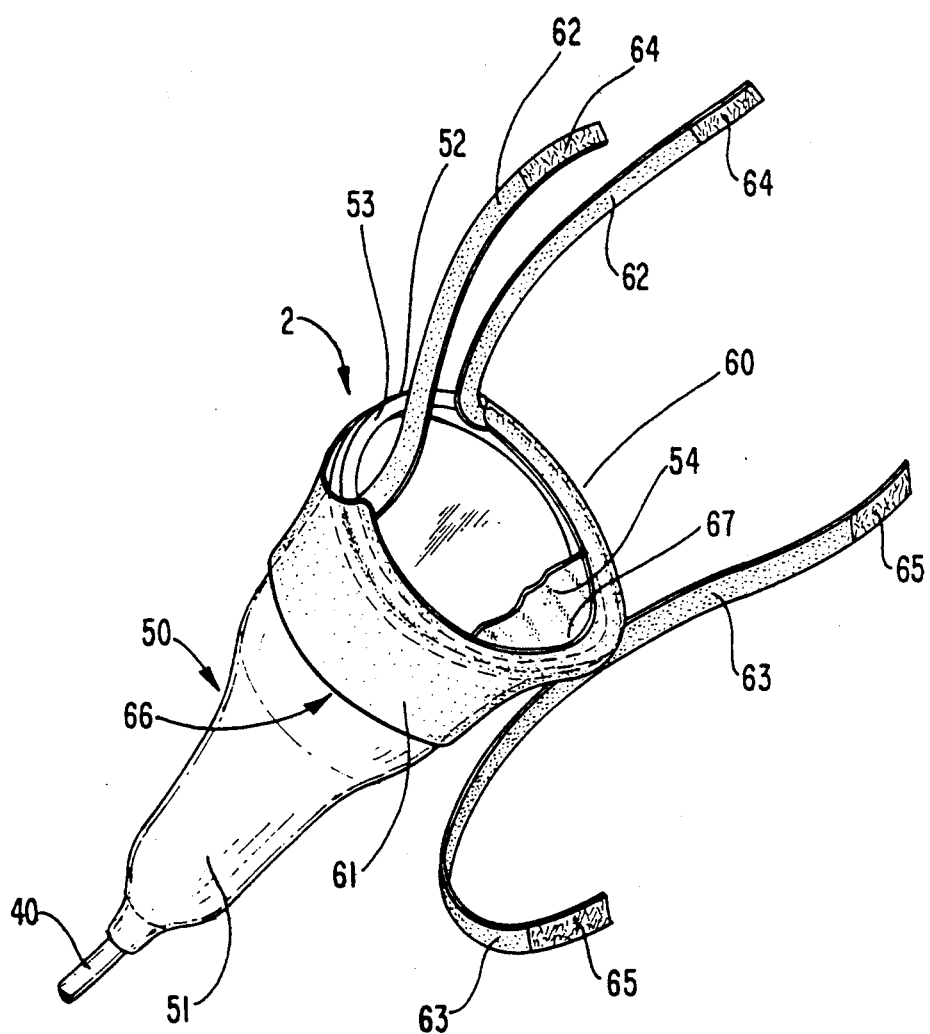
FIG. 6 is a perspective view of a second preferred embodiment of the present invention.

FIG. 6 illustrates in a side perspective view the sheath 50 and waist belt assembly 60 of a second preferred embodiment of an external catheter system 2 constructed in accordance with the teachings of the present invention. The waist belt assembly 60 is of unitary construction and slip fits about said sheath 50. The sheath 50 is constructed with an upper portion 51 and a lower portion 52 substantially similar as described for sheath 10 of the first preferred embodiment shown in FIGS. 1-3. Sheath 50 further includes a scrotum retainer 54 fixedly attached at the lower arc of the peripheral lip 53 of said sheath 50, said scrotum retainer 54 being preferably formed of flaccid material disposed between opposing sides of said lip 53 in a manner to permit said scrotum retainer 54 to conform to the shape of the rearpart of the male scrotum. The waist belt assembly 60 of the second preferred embodiment comprises a sheath cup 61, paired waist belt straps 62 fixedly attached to the upper portion of sheath cup 61 and paired buttock straps 63 fixedly attached to the lower portion of said sheath cup 61. Waist belt assembly 60 is preferably formed from resilient elastic material, said waist belt straps 62 being provided to attach to each other generally about the waist of the user and said buttock straps 63 being provided to attach about the thighs of the user below the buttock. Hook and loop tape fasteners 64, 65 are respectively attached to the ends of waist belt straps 62 and buttock straps 63. The sheath cup 61 is formed with respective upper and lower orifices 66, 67 through which said sheath 50 is slip fit and retained within said sheath cup 61. The edge of said upper orifice 67 extends beyond the edge of the lip 53 of said sheath thereby providing padding means to prevent rubbing of the user's body against the sheath 50 and the creation of sores.

The external catheter system 1 of the present invention provides improved means for leak resistant and sanitary urine collection. The sheath of the present invention also provides means to prevent withdrawal of the male genitalia within the body. While preferred embodiments of the present invention have been described, various changes and modifications may be made without departing from the spirit and scope of the disclosure as hereinafter claimed. For example, alternative sheath attachment means may be utilized in lieu of attachment clips 26 and attachment tabs 15a, 15b. Such changes and modifications are intended to be within the scope of the present invention and covered by the appended claims.

Therefore in view of the foregoing, I claim:

1. An external urine catheter system for males adapted to fit and be worn around the waist and the lower part of the male abdomen comprising in combination;

a substantially tubular sheath for receipt of male genitalia, said sheath including an upper portion and a lower portion, said upper portion being adapted to fit at one end adjacent to the pubic area of the male user providing a scrotal support portion, said lower portion being integrally formed at the distal end of said upper portion a providing penis receptacle portion, said lower portion being formed with a smaller diameter than said upper portion that decreases from the adjoining end to its distal end, said sheath having an opening extending longitudinally throughout its body, said opening generally conforming to a shape of a male scrotum within said scrotal support portion and to the shape of a the male penis within said penis receptacle portion, said sheath including a scrotum bar extending laterally across the lower part of the end of said upper portion adjacent to the pubic area and waist belt attachment means integrally formed at the end of said scrotal support portion that is disposed adjacent to the body of the user, said scrotum bar being formed from soft rubber material, a waist belt assembly selectively attachable to said sheath providing means to secure said sheath to the body of the user, said waist belt assembly including a waist belt having two ends, a pair of sheath straps and a pair of thigh straps, said waist belt including adjustable belt closure means, said sheath straps and said thigh straps being fixedly and respectively attached at one end to the sides of said waist belt and selectively attachable at the opposite end to said tubular sheath, said sheath straps being disposed to fit across the upper front portion of the thighs of the user, said thigh straps being disposed to fit around the back portion of the thighs of the user passing under the buttocks to the crotch of the user, a urine collector comprising a flexible container including a urine inlet receptacle and a collector disposal port having means for selectively sealing said disposal port, and a length of hollow tubing interconnecting said sheath and said urine collector comprising a length of hollow tubing sealingly engageable with the urine inlet receptacle of said urine collector at one end and sealingly engageable with the opening of said sheath at the opposite end.

2. An external urine catheter system as described in claim 1 wherein said waist belt assembly comprises a unitary construction of belts and straps including a waist belt, a pair of frontal sheath straps and a pair of thigh straps, said waist belt, sheath straps and thigh straps being formed from resilient elastic material, said waist belt including a hook and loop tape fastener fixedly attached to the free ends of said waist belt, the hook portion of said fastener being attached to the inside surface of one end of said waist belt and the loop portion of said fastener being attached to the outside surface of the other end of said waist belt, said frontal sheath straps and thigh straps being fixedly attached at one end to the inside surface of the waist belt by stitching means, said frontal sheath straps being attached to the forward side portions of said waist belt extending angularly toward the front of said waist belt assembly and said thigh straps being attached to the rearward side portions of said waist belt extending angularly toward the rear of said waist belt assembly, the free ends of said frontal sheath straps and said thigh straps being looped and stitched to form a closed loop wherein attachment clips are disposed for engagement with said sheath, said attachment clips being formed of plastic or similar lightweight material.

3. An external urine catheter system as described in claim 1 wherein said waist belt assembly comprises a two-piece belt assembly including a waist belt and an integrally constructed pair of frontal sheath straps fixedly attached and respectively disposed on each side of said waist belt, and a separate and singular thigh strap, said thigh strap being adaptable to be worn about the outer portions of the thighs and below the buttocks of the user, said frontal sheath straps and said thigh strap being adaptable for selective attachment to said sheath, said waist belt, frontal sheath straps and thigh strap being formed from resilient elastic material.

4. An external urine catheter system as described in claim 1 wherein the upper portion of said sheath is generally formed in the shape of a bottomless cup having an arcuate lip circumscribing said opening, said lip having a lip prolongation formed to one side of said lip which extends outwardly from the upper portion of said sheath, said lip prolongation protruding into the crotch of the user when worn, said scrotum bar being disposed adjacent to said lip prolongation being fixedly attached to opposing sides of said lip, said sheath further including paired upper and lower attachment tabs which extend outwardly from said lip, said upper attachment tabs extending from the upper sides of said lip and said lower attachment tabs extending from the sides of said lip prolongation.

5. An external urine catheter system as described in claim 1 wherein said urine collector comprises a flexible box having a rigid top member and a rigid bottom member, said top member having a urine inlet receptacle formed therein for receipt of said sheath draining tubing in sealingly engagement, and a side member of said box having a collector disposal port formed therein, said disposal port comprising a threaded port neck and a complimentarily threaded port neck cap provided to selectively seal said disposal port, said urine collector providing means for collection of urine from said sheath and means for staging of collected urine for treatment prior to ultimate disposal.

6. An external urine catheter system for males adapted to fit and be worn around the waist and the lower part of the male abdomen comprising in combination;

a substantially tubular sheath for receipt of male genitalia, said sheath having foam padding disposed throughout its body adjacent to the inner walls of said sheath and an opening extending longitudinally therethrough, said padding conforming to the contours of said sheath; said sheath including an upper portion and a lower portion, said upper portion providing scrotum receptacle means being generally formed in the shape of a bottomless cup having an arcuate lip circumscribing said opening, said lip having a lip prolongation formed to one side of said lip which extends outwardly from the upper portion of said sheath, said lip prolongation protruding into a crotch of a user when worn, said upper portion being adapted to fit at one end adjacent to the pubic area of the male user providing scrotal support means, said lower portion being integrally formed at the distal end of said upper portion providing penis receptacle means, said lower portion being formed with a smaller diameter than said upper portion that decreases from the adjoining end to its distal end; said sheath including a scrotum bar fixedly attached to opposing sides of said lip adjacent to said lip prolongation, said scrotum bar being formed from a dense soft rubber material; said opening generally conforming to the shape of the male scrotum within said scrotal support portion and to the shape of a male penis within said penis receptacle portion; said sheath including integrally formed paired upper and lower waist belt attachment tabs which extend outwardly from said lip, said upper attachment tabs extending from the upper sides of said lip and said lower attachment tabs extending from the sides of said lip prolongation;

a unitary waist belt assembly selectively attachable to said sheath providing means to secure said sheath to the body of the user, said waist belt assembly including a waist belt having two ends, a pair of frontal sheath straps and a pair of thigh straps, said waist belt, sheath straps and thigh straps being formed from resilient elastic material, said waist belt including adjustable belt closure means comprising a hook and loop tape fastener fixedly attached to the free ends of said waist belt, the hook portion of said fastener being attached to the inside surface of one end of said waist belt and the loop portion of said fastener being attached to the outside surface of the other end of said waist belt, said sheath straps and said thigh straps being fixedly and respectively attached at one end to the sides of said waist belt by stitching means and selectively attachable at the opposite end to said tubular sheath, said frontal sheath straps being attached to the forward side portions of said waist belt extending angularly toward the front of said waist belt assembly and said thigh straps being attached to the rearward side portions of said waist belt extending angularly toward the rear of said waist belt assembly, the free ends of said frontal sheath straps and said thigh straps being looped and stitched to form a closed loop wherein attachment clips are disposed for engagement with said sheath, said attachment clips being formed of plastic or similar lightweight material, said sheath straps being disposed to fit across the upper front portion of the thighs of the user, said thigh straps being disposed to fit around the back portion of the thighs of the user passing under the buttocks to the crotch of the user, the attachment clips of said frontal sheath straps being provided for engagement with the upper attachment tabs of said sheath and the attachment clips of said thigh straps being provided for engagement with the lower attachment tabs of said sheath;

a urine collector comprising a flexible box having a rigid top member and a rigid bottom member, said top member having a urine inlet receptacle formed therein, a side member of said box having a collector disposal port formed therein, said disposal port comprising a threaded port neck and a complimentarily threaded port neck cap provided to selectively seal said disposal port, said urine collector providing means for collection of urine from said sheath and means for staging of collected urine for treatment prior to ultimate disposal; and a length of hollow tubing interconnecting said sheath and said urine collector comprising a length of hollow tubing sealingly engageable with the urine inlet receptacle of said urine collector at one end and sealingly engageable with the opening of said sheath at the opposite end.

7. An external urine catheter system for males adapted to fit and be worn around the waist and the lower part of the male abdomen comprising in combination;

a substantially tubular sheath for receipt of male genitalia, said sheath having foam padding disposed throughout its body adjacent to the inner walls of said sheath and an opening extending longitudinally therethrough, said padding conforming to the contours of said sheath; said sheath including an upper portion and a lower portion, said upper portion providing scrotum receptacle means being generally formed in the shape of a bottomless cup having an arcuate lip circumscribing said opening, said lip having a lip prolongation formed to one side of said lip which extends outwardly from the upper portion of said sheath, said lip prolongation protruding into the crotch of the user when worn, said upper portion being adapted to fit at one end adjacent to a pubic area of a male user providing scrotal support means, said lower portion being integrally formed at the distal end of said upper portion providing penis receptacle means, said lower portion being formed with a smaller diameter than said upper portion that decreases from the adjoining end to its distal end; said sheath including a scrotum bar fixedly attached to opposing sides of said lip adjacent to said lip prolongation, said scrotum bar being formed from a dense soft rubber material; said opening generally conforming to the shape of a male scrotum within said scrotal support portion and to the shape of a male penis within said penis receptacle portion; said sheath including integrally formed paired upper and lower waist belt attachment tabs which extend outwardly from said lip, said upper attachment tabs extending from the upper sides of said lip and said lower attachment tabs extending from the sides of said lip prolongation;

a two-piece waist belt assembly selectively attachable to said sheath providing means to secure said sheath to the body of the user, said waist belt assembly including a waist belt comprising a pair of ends and a forward position and an integrally constructed pair of frontal sheath straps fixedly attached and respectively disposed on each side of said waist belt, and a separate and singular thigh strap, said thigh strap being adaptable to be worn about the outer portions of the thighs and below the buttocks of the user, said waist belt including adjustable belt closure means comprising a hook and loop tape fastener fixedly attached to the free ends of said waist belt, the hook portion of said fastener being attached to the inside surface of one end of said waist belt and the loop portion of said fastener being attached to the outside surface of the other end of said waist belt, said sheath straps being fixedly and respectively attached at one end to the sides of said waist belt by stitching means and selectively attachable at the opposite end to said tubular sheath, said frontal sheath straps being attached to the forward side portions of said waist belt extending angularly toward the front of said waist belt assembly, said frontal sheath straps and said thigh strap being adaptable for selective attachment to said sheath, the free ends of said frontal sheath straps and said thigh strap being looped and stitched to form a closed loop wherein attachment clips are disposed for engagement with said sheath, said attachment clips being formed of plastic or similar lightweight material, said sheath straps being disposed to fit across the upper front portion of the thighs of the user, said waist belt, frontal sheath straps and thigh strap being formed from resilient elastic material;

a urine collector comprising a flexible box having a rigid top member and a rigid bottom member, said top member having a urine inlet receptacle formed therein, a side member of said box having a collector disposal port formed therein, said disposal port comprising a threaded port neck and a complimentarily threaded port neck cap provided to selectively seal said disposal port, said urine collector providing means for collection of urine from said sheath and means for staging of collected urine for treatment prior to ultimate disposal; and a length of hollow tubing interconnecting said sheath and said urine collector comprising a length of hollow tubing sealingly engageable with the urine inlet receptacle of said urine collector at one end and sealingly engageable with the opening of said sheath at the opposite end.

8. An external urine catheter system for males adapted to fit and be worn around the waist and the lower part of the male abdomen comprising in combination;

a substantially tubular sheath for receipt of male genitalia, said sheath having foam padding disposed throughout its body adjacent to the inner walls of said sheath and an opening extending longitudinally therethrough, said padding conforming to the contours of said sheath; said sheath including an upper portion and a lower portion, said upper portion providing scrotum receptacle means being generally formed in the shape of a bottomless cup having an arcuate lip circumscribing said opening, said sheath including a scrotum retainer formed of flaccid material disposed between opposing sides of said lip in a manner to permit conforming of said retainer to the shape of a male scrotum;

a unitary waist belt assembly formed of resilient elastic material, said waist belt assembly comprising a sheath cup, paired waist belt straps and paired buttock straps, said waist belt straps being fixedly attached to the upper portion of said sheath cup and said buttock straps being fixedly attached to the lower portion of said sheath cup, said sheath cup having an upper and lower orifice, said sheath being receivable within said upper and lower orifices in slip fit attachment having the edge of said upper orifice extending beyond the lip of said sheath, said waist belt straps and said buttock straps having hook and loop tape fasteners attached at the ends of said respective straps;

a urine collector comprising a flexible box having a rigid top member and a rigid bottom member, said top member having a urine inlet receptacle formed therein, a side member of said box having a collector disposal port formed therein, said disposal port comprising a threaded port neck and a complimentarily threaded port neck cap provided to selectively seal said disposal port, said urine collector providing means for collection of urine from said sheath and means for staging of collected urine for treatment prior to ultimate disposal; and a length of hollow tubing interconnecting said sheath and said urine collector comprising a length of hollow tubing sealingly engageable with the urine inlet receptacle of said urine collector at one end and sealingly engageable with the opening of said sheath at the opposite end.

9. An external urine catheter system for males adapted to fit and be worn around the waist and the lower part of the male abdomen comprising a substantially tubular sheath for receipt of male genitalia, said sheath having a scrotum bar for retention of the scrotum within said sheath;

means to secure said sheath to the waist and the lower part of the abdomen of a wearer; and means to collect urine from said sheath.

10. An improvement in external urine catheters for males of the type in which male genitalia is received within a substantially tubular sheath, the improvement comprising a scrotum bar disposed in said sheath in a manner to retain the scrotum within said sheath.

* * * * *